United States Patent [19]

Panayotatos

[11] Patent Number: 5,349,056
[45] Date of Patent: Sep. 20, 1994

[54] MODIFIED CILIARY NEUROTROPHIC FACTORS

[75] Inventor: Nikos Panayotatos, Orangeburg, N.Y.

[73] Assignee: Regeneron Pharmaceuticals, Tarrytown, N.Y.

[21] Appl. No.: 959,284

[22] Filed: Oct. 9, 1992

[51] Int. Cl.$^5$ .................... A61K 37/36; A61K 37/10; C12P 21/06
[52] U.S. Cl. .................... 530/399; 435/69.1; 435/69.4
[58] Field of Search .................... 530/399; 514/12; 435/69.1, 69.4

[56] References Cited
U.S. PATENT DOCUMENTS 4,997,929  3/1991  Collins et al. .................... 536/27

OTHER PUBLICATIONS

Lin et al. *Science* 246: 1023–1025 (1989).
Alber *Ann Rev Biochem* 58:765–98 (1989).

*Primary Examiner*—Garnette D. Draper
*Assistant Examiner*—Shelly Guest Cermak
*Attorney, Agent, or Firm*—Gail Kempler

[57] ABSTRACT

Modified ciliary neurotrophic factors and methods for their production and therapeutic use. Also described is a method of screening for novel therapeutic proteins by determining altered electrophoretic binding properties.

3 Claims, 4 Drawing Sheets

Fig. 1A

```
              Nhe1                    Alw N1                                        Hind3
     10         20         30         40         50         60         70         80         90        100
MAFTEHSPLTPHRRDLCSRSIWLARKIRSDLTALTESYVKHQGLNKNINLDSADGMPVASTDQWSELTEAERLQENLQAYRTFHVLLARLLEDQQVHFTP
hu
rt  ...A.QT...L.................................................V.V..R..M....................QGM.TK......R.....
rb  ...M..A....E....T.........................................V..V.M............IM...................
ms  ...A.Q..L...................M......S..V....M..........R..M........-QGMLT......R.....
ch  ..AADTPSA.LRHH....G.R...M...V.D.LDI..ER...DAS.SVAAV.V.T.AVER.A.Q.GTQ..LD..A...A.RT...QM..E.RELLGD
```

Fig. 1B

```
     10         20         30         40         50         60         70         80         90        100
186  ...A.QT...L.........................................................................QGM.TK......R.....
187  ......................................M.................................................
188  ...A.QT...L.........................M...........V.V..R..M.................QGM.TK......R.....
189  ......................................M...........V.V..R..M.................QGM.TK......R.....
192  ......................................M...........V.V..R..M.................QGM.TK......R.....
218  ..................................................V.V..R..M...............................
219  ......................................................V.V..R..M...............................
222  ...................................................V.V..R..M...............................
223  ..........................................................M...............................
228  .................................................V...R...................................
```

Fig.1A-1

```
                                          BsaI                                                  BamH1
        110        120        130        140        150        160        170        180        190        200
hu  TEGDFHQAIHTLLLQVAAFAYQIEELMILLEYKIPRNEADGMPINVGDGGLFEKKLWGLKVLQELSQWTVRSIHDLRFISSHQTGIPARGSHYIANNKKM
rt  .....M..S......L....V....Q..E......AT.........................V....M.S.LE...G.KD.Q.
rb  A...HF..........V...CN.PKD...T.V-I.GD..........H.............V..C...H.....D.E.
ms  .....T-.S....L..A..Q.-V......VTI..............................V...HM.S.H-..G....Q.
ch  .DAELGP.LAAM....S..V.HL..LE-.SRGAPA.EGSE.PAPPRLS..Q..R..R..R..A..A..VR..QL.K.G---.GS.AALGLPESQ-
```

MODIFIED CILIARY NEUROTROPHIC FACTORS

BACKGROUND OF THE INVENTION

The present invention relates to CNTF-related polypeptides.

Ciliary neurotrophic factor (CNTF) is a protein that is required for the survival of embryonic chick ciliary ganglion neurons in vitro (Manthorpe et al., 1980, J. Neurochem. 34:69–75). The ciliary ganglion is anatomically located within the orbital cavity, lying between the lateral rectus and the sheath of the optic nerve; it receives parasympathetic nerve fibers from the oculomotor nerve which innervates the ciliary muscle and sphincter pupillae.

Over the past decade, a number of biological effects have been ascribed to CNTF in addition to its ability to support the survival of ciliary ganglion neurons. CNTF is believed to induce the differentiation of bipotential glial progenitor cells in the perinatal rat optic nerve and brain (Hughes et al., 1988, Nature 335:70–73). Furthermore, it has been observed to promote the survival of embryonic chick dorsal root ganglion sensory neurons (Skaper and Varon, 1986, Brain Res. 389:39–46). In addition, CNTF supports the survival and differentiation of motor neurons, hippocampal neurons and presympathetic spinal cord neurons [Sendtner, et al., 1990, Nature 345: 440–441; lp, et al. 1991, J. Neurosci. 11:3124–3134; Blottner, et al. 1989, Neurosci. Lett. 105:316–320].

Recently, CNTF has been cloned and synthesized in bacterial expression systems, as described by Masiakowski, et al., 1991, J. Neurosci. 57:1003–1012 and in International Publication No. WO 91/04316, published on Apr. 4, 1991, which are incorporated by reference in their entirety herein.

The receptor for CNTF (termed "CNTFRα") has been cloned, sequenced and expressed [see Davis, et al. (1991) Science 253:59–63]. CNTF and the haemopoetic factor known as leukemia inhibitory factor (LIF) act on neuronal cells via a shared signaling pathway that involves the IL-6 signal transducing component gp130 as well as a second, β-component (know as LIFR β); accordingly, the CNTF/CNTF receptor complex can initiate signal transduction in LIF responsive cells, or other cells which carry the gp130 and LIFRβ components [Ip, et al. (1992) Cell 69:1121-1132].

In addition to human CNTF, the corresponding rat (Stöckli et al., 1989, Nature 342:920–923), and rabbit (Lin et al., 1989, J. Biol. Chem. 265:8942–8947) genes have been cloned and found to encode a protein of 200 amino acids, which share about 80% sequence identity with the human gene. Both the human and rat recombinant proteins have been expressed at exceptionally high levels (up to 70% of total protein) and purified to near homogeneity.

Despite their structural and functional similarity, recombinant human and rat CNTF differ in several respects. The biological activity of recombinant rat CNTF in supporting survival and neurite outgrowth from embryonic chick ciliary neurons in culture is four times better than that of recombinant human CNTF [Masiakowski et al., (1991), J. Neurochem. 57:1003–1012]. Further, rat CNTF has a higher affinity for the human CNTF receptor than does human CNTF.

A surprising difference in the physical properties of human and rat CNTF, which are identical in size, is their different mobility on SDS gels. This difference in behaviour suggests the presence of an unusual structural feature in one of the two molecules that persists even in the denatured state (Masiakowski et al., 1991, id.).

Mutagenesis by genetic engineering has been used extensively in order to elucidate the structural organization of functional domains of recombinant proteins. Several different approaches have been described in the literature for carrying out deletion or substitution mutagenesis. The most successful appear to be alanine scanning mutagenesis [Cunningham and Wells (1989), Science 244:1081–1085]and homolog-scanning mutagenesis [Cunningham et al., (1989), Science 243:1330–1336]. These approaches helped identify the receptor binding domains of growth hormone and create hybrid proteins with altered binding properties to their cognate receptors.

SUMMARY OF THE INVENTION

An object of the present invention is to provide novel CTNF-related neurotrophic factors.

A further object of the present invention is to provide a method for identifying CNTF-related factors, other than those specifically described herein, that have improved therapeutic properties.

These and other objects are achieved in accordance with the invention, whereby amino acid substitutions in human CNTF protein enhance its therapeutic properties. In one embodiment, alterations in electrophoretic mobility are used to initially screen potentially useful modified CNTF proteins.

In a preferred embodiment, the amino acid glutamine in position 63 of human CNTF is replaced with arginine or another amino acid which results in a modified CNTF molecule with improved biological activity.

BRIEF DESCRIPTION OF THE DRAWINGS

FIG. 1. alignment of CNTF protein sequences. A. Human, [Seq ID No.:1] rat, [Seq ID No.:2] rabbit mouse [Seq ID No.:4] and chicken [Seq ID No.:5] (Leung, et al., 1992, Neuron 8:1045-1053) sequences. Dots indicate residues found in the human sequence. Panel B. Modified CNTF molecules (186 [SEQ ID No.:6], 187 [SEQ ID No.:7], 188 [SEQ ID No.: 8], 189 [SEQ ID No.: 9], 192 [SEQ ID No. 10], 218 [SEQ ID No.: 11], 219 [SEQ ID No.: 12], 222 [SEQ ID No.: 13], 223 [SEQ ID No. 14] and 228 [SEQ ID No.: 15] showing human CNTF amino acid residues (dots) and rat CNTF (residues shown). The name of the purified recombinant protein corresponding to each sequence is shown on the left.

FIG. 2. Mobility of human, rat and several modified CNTF molecules on reducing SDS-15% polyacrylamide gels. Purified recombinant proteins were loaded as indicated. Markers of the indicated MW were loaded on lane M.

DETAILED DESCRIPTION OF THE INVENTION

Figure 3A:
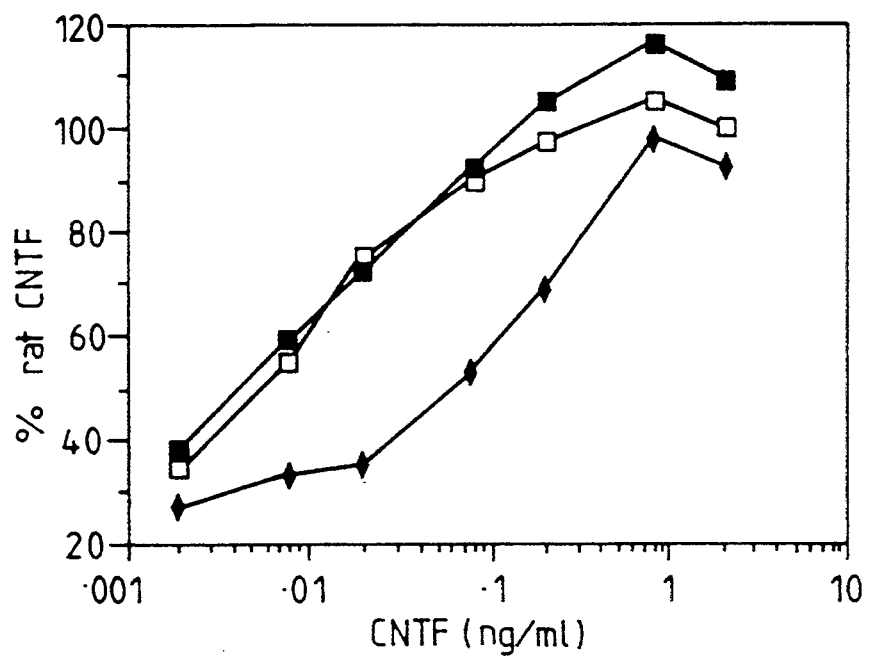
FIG. 3A and 3B. Biological activity of two modified CNTF molecules. A human CNTF (filled diamonds), rat CNTF (open squares), and RPN219 (filled squares). B. human CNTF (filled diamonds), rat CNTF (open squares), and RPN228 (filled squares). Dose response of dissociated E8 chick ciliary neurons surviving at the indicated protein concentration, as a percentage of the number of neurons surviving in the presence of 2 ng/ml rat CNTF. Each experimental point represents the mean of three determinations.

The present invention is based, in part, on the initial finding that recombinant rat CNTF binds more efficiently to the human CNTF receptor than does recombinant human CNTF and the subsequent discovery that amino acid substitutions which cause human CNTF to more closely resemble rat CNTF result in enhanced binding of the modified CNTF to the human CNTF receptor and concomitant enhanced biological activity.

In a preferred embodiment, alteration of a single amino acid of the human CNTF protein results in a signficant enhancement of the ability of the protein to promote the survival and outgrowth of ciliary ganglion neurons.

Recombinant human and rat CNTF have the same number of amino acids (199) and similar mass (NW 22,798 and 22,721 respectively, after removal of the N-terminal methionine). Yet, on reducing SDS-PAGE gels, recombinant human CNTF migrates as a protein of MW=27,500, whereas rat CNTF migrates with the expected mobility. In addition, human CNTF has four times lower biological activity towards chick ciliary ganglion (CG) neurons than rat CNTF and the human protein competes for binding to the human or the rat receptor on cell surfaces much less effectively than rat CNTF.

The above observation led to a directed effort to identify the region on the CNTF molecule responsible for these differences. This method involved the exchange, by genetic engineering methods, of parts of the human CNTF sequence with the corresponding rat CNTF sequence and vice versa. To achieve this, advantage was taken of restriction sites that are common to the two CNTF genes and unique in their corresponding expression vectors. When necessary, such sites were engineered in one or the other of the two genes in areas that encode the same protein sequence. With this approach, expression vectors were obtained for each of the modified proteins shown in FIG. 1. After isolating the individual proteins to at least 60% purity, their properties, as compared to those of human and rat CNTF were determined.

Because the electrophoretic mobilities of human and rat CNTF differ significantly, the effect of each amino acid substitution was monitored initially by making a determination of the effect of such change on the mobility of the protein. As described herein, electrophoretic mobility data indicated that all of the modified human CNTF molecules that migrated to the same position as rat CNTF had the single amino acid substitution Gln63→Arg (Q63→R).

Modified human CNTF proteins that demonstrated an electrophoretic mobility similar to that of the rat CNTF molecule were subsequently examined for biological activity and receptor binding.

CNTF is characterized by its capacity to support the survival of dissociated ciliary neurons of E8 chick embryos. By this criterion, purified recombinant rat CNTF is as active as the native protein from rat, but four times more active than recombinant human CNTF [Masiokowski, et al. (1991), id]. The same assay was utilized to determine the biological activity of the altered molecules prepared as described above. As described herein, all of the modified CNTF molecules that had the Q63→R substitution exhibited an increased ability to support the survival of ciliary ganglion neurons as compared to the parent human CNTF protein. Such results indicated a strong correlation between alteration of the electrophoretic mobility and enhanced biological properties.

In addition to measuring the biological effect of modifications made to human CNTF, an indication of the potential biological activity of each of the molecules may also be obtained by determining the effect of each modification on the ability of the molecules to bind to the CNTF receptor.

In one embodiment, the ability of the modified human CNTF proteins to compete with rat CNTF for binding to rat superior cervical ganglia neurons (SCGs) is measured. As described herein, human CNTF is about 90 times less potent is displacing $^{125}$I-labelled rat CNTF binding from these cells than unlabelled rat CNTF. Several of the modified human CNTF proteins described herein, however, are more potent than the human CNTF in displacing the rat protein. All of the molecules described herein that had such increased competitive binding ability were molecules that exhibited altered electrophoretic mobility, wherein the molecules migrated in a manner similar to rat CNTF.

In another embodiment, cells, such as MG87 fibroblasts, are engineered to express the human CNTF receptor α-component and such cells are used to assay the binding capability of the modified protein to the human receptor. Human CNTF is about 12 times less potent than rat CNTF in competing with $^{125}$I-labelled rat CNTF for binding to the human CNTF receptor. Several of the modified human CNTF molecules described herein, including all of those with electrophoretic mobility that resemble rat rather than human CNTF, were more potent than human CNTF in competing with binding of $^{125}$I-rat CNTF to the cells expressing the human CNTF receptor.

In another embodiment, an animal model with demonstrated utility in providing an indication of the ability of certain growth and other factors to prevent degeneration of retinal photoreceptors may be used to assess the therapeutic properties of the modified CNTF molecules according to the present invention. As described in Example 4, hCNTF (Gln63→Arg) has a ten-fold higher ability than recombinant human CNTF to prevent degeneration of photoreceptors in a light-induced damage model of retinal degeneration.

Thus, according to the invention, certain amino acid substitutions in the human CNTF protein result in modified human CNTF proteins that exhibit enhanced binding to the human CNTF receptor and therefore, would be expected to have enhanced therapeutic properties.

The modified CNTF molecules useful for practicing the present invention may be prepared by cloning and expression in a prokaryotic or eukaryotic expression system. The recombinant neurotrophin gene may be expressed and purified utilizing any number of methods. The gene encoding the factor may be subcloned into a bacterial expression vector, such as for example, but not by way of limitation, pCP110.

The recombinant factors may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, conventional ion exchange chromatography, hydrophobic interaction chromatography, reverse phase chromatography or gel filtration may be used.

According to the present invention, modified CNTF molecules produced as described herein, or a hybrid or mutant thereof, may be used to promote differentiation, proliferation or survival in vitro or in vivo of cells that are responsive to CNTF, including cells that express receptors of the CNTF/IL-6/LIF receptor family, or any cells that express the appropriate signal transducing component, as described, for example, in Davis, et al (1992) Cell 69:1121–1132. Mutants or hybrids may alternatively antagonize cell differentiation or survival.

The present invention may be used to treat disorders of any cell responsive to CNTF or CNTF/CNTF receptor complex. In preferred embodiments of the invention, disorders of cells that express members of the CNTF/IL-6/LIF receptor family may be treated according to these methods. Examples of such disorders include but are not limited to those involving the following cells: leukemia cells, hematopoietic stem cells, megakaryocytes and their progenitors, DA1 cells, osteoclasts, osteoblasts, hepatocytes, adipocytes, kidney epithelial cells, embryonic stem cells, renal mesangial cells, T cells, B cells, etc.

As described herein, applicants have determined that altered electrophoretic mobility provides a reliable method for screening for proteins with enhanced biological activity or ligand binding capability. Accordingly, the method described herein may have general applicability in screening for novel therapeutic proteins. Such a method would involve determining the electrophetic mobility of a wild-type human protein, introducing amino acid substitutions into the wild-type human protein and identifying as potential candidates substituted proteins that have altered electrophoretic mobility as compared to the electrophoretic mobility of the wild-type protein. Such substitute proteins could be further tested to determine their biological activity and/or binding affinity. Potential amino acid substitutions could be based, for example, on comparable sequences from homologous proteins of non-human species.

One skilled in the art will recognize that other alterations in the amino acid sequence of CNTF may provide enhanced properties to the molecule. One skilled in the art will also recognize that CNTF homologues from other species, i.e. mouse, rabbit and chicken, may also have enhanced properties in treating human disease or disorders. Thus, the present invention contemplates a method of identifying novel neurotrophic factors, whereby neurotrophic factors from species other than human are identified and assayed with respect to their ability to bind the human receptor as well their biological activity in human cell lines and in vivo systems. When neurotrophic factors from animal species are identified which have novel properties, methods known to those in the art, such as those described herein, can be used to interchanged portions of the human factor with the animal-derived factor to create novel neurotrophic factors with enhanced therapeutic properties.

EXAMPLES

EXAMPLE 1

Electrophoretic Mobility or Modified Human CNTF Molecules

Material and Methods

Preparation of Modified CNTF molecules

Bacterial Strains and Plasmids

*E. coli* K-12 RFJ26 is strain that overproduces the lactose operon repressor.

The expression vectors pRPN33, which carries the human CNTF gene and pRPN110 which carries the rat CNTF gene are nearly identical (Masiakowski, et al. 1991, id.).

Plasmid pRPN219 was constructed by first digesting pRPN33 with the restriction enzymes Nhe1 plus Hind3 and gel purifying the 4,081 bp fragment. The second, much smaller fragment which codes for part of the human CNTF gene was subsequently replaced with an 167 bp Nhe1-Hind3 fragment that was obtained by PCR amplification from the rat gene using the primers RAT-III-dniH: [Seq ID. No: 16] 5'ACGGTAAGCT TGGAGGTTCTC 3'; and RAT-Nhe-I-M. [Seq ID. No: 17] 5' TCTATCTGGC TAGCAAGGAA GATTCGTTCA GACCTGACTG CTCTTACG3'.

Plasmid pRPN228 was constructed in the same manner as pRPN219, except that the 167 bp replacement fragment was amplified using the DNA primers RAT-III-dniH-L-R [Seq. ID. No. 18]: AAG GTA CGA TAA GCT TGG AGG TTC TCT TGG AGT CGC TCT GCC TCA GTC AGC AGC TCA CTC CAA CGA TCA GTG 3' and Rat-Nhe-I [Seq ID No. 19]5' TCT ATC TGG CTA GCA AGG AAG 3'.

Plasmids pRPN186, pRPN187, pRPN188, pRPN189, pRPN192, pRPN218, and pRPN222 were generated by similar means or by direct exchange of DNA fragments using the unique restriction sites shown in FIG. 1.

The identity of all plasmids was confirmed by restriction analysis and DNA sequencing.

Protein Purification

Induction of protein synthesis, selective extraction, solubilization and purification from inclusion bodies were as described for rat and human CNTF (Masiakowski, et al, 1991, id.) except that gel filtration was occasionally used instead or in addition to ion exchange chromatography. Alternatively, proteins were purified from the supernatants of cell lysates by streptomycin and ammonium sulfate fractionation, followed by column chromatography, as described for other proteins (Panayotatos et al., 1989, J. Biol. Chem. 264:15066–15069). All proteins were isolated to at least 60% purity.

Conditions for enzymatic reactions, DNA electrophoresis and other techniques used in these studies have been described in detail (Panayotatos, N. 1987, Engineering an Efficient Expression System in Plasmids: A practical approach (Hardy, K. G. ed.) pp 163–176, IRL Press, Oxford, U.K.).

Results

The mobilities of human, rat and several chimeric CNTF molecules on reducing SDS-polyacrylamide gels are shown in FIG. 2. The chimeric molecules RPN186, RPN189, RPN218 and RPN 228 exhibit mobilities comparable to rat CNTF, whereas RPN187, RPN188, RPN192 and RPN222 exhibit mobilities comparable to human CNTF. Cross-reference of these results to the aligned sequence of these proteins in FIG. 1 reveals that all proteins carrying an arginine residue at position 63 (R63) display the mobility of rat CNTF. In the case of RPN228, this single amino acid substitution (Q63→R) is sufficient to confer to human CNTF the normal mobility of rat CNTF.

FIG. 2 also provides a measure of the purity of the different recombinant proteins. By visual inspection, purity varies from 60% for RPN189 to better than 90% for RPN228.

EXAMPLE 2

Measurement of Binding Activity of Modified CNTF Molecules

Materials and Methods

Preparation of $^{125}$I-CNTF

Recombinant rat CNTF (28 μg) in 37 μl 0.2M sodium borate buffer, pH 8.5 was transfered to a vial containing 4 mCi, (2,000 Ci/mmole; NEN) of $^{125}$I and reagent (Bolton and Hunter, 1973, Biochem J. 133: 529–539) which had been dried under a gentle stream of nitrogen. Reactions were incubated for 45 min at 0° C. followed by 15 min at room temperature and terminated by the addition of 30 ml of 0.2M glycine solution. After 15 min, 0.2 ml PBS containing 0.08% gelatin was also added and the mixture was passed through a Superdex-75 column (Pharmacia) to separate the labelled monomeric CNTF from dimeric and other multimeric derivatives. Percentage of incorporation was typically 20%, as determined by thin layer chromatography and the specific activity was typically around 1,000 Ci/mmole. The monomeric $^{125}$I-CNTF was stored at 4° C. and used up to one week after preparation. As a test of structural and conformational integrity, $^{125}$I-CNTF (approximately 10,000 cpm was mixed with a 5 μg unlabelled CNTF and analyzed by native gel eletrophoresis. One major band was visible by either Coomassie staining or autoradiography. $^{125}$I-CNTF also showed comparable activity to native CNTF in supporting survival of E8 chick ciliary neurons in culture.

Tissue Culture Techniques

Superior cervical ganglia (SCG) from neonatal rats were treated with trypsin (0.1%), mechanically dissociated and plated on a polyornithine (30 μg/ml) substratum. Growth medium consisted of Ham's nutrient mixture F12 with 10% heat-inactivated fetal bovine serum (Hyclone), nerve growth factor (NGF) (100 ng/ml), penicillin (50 U/ml) and streptomycin (50 μg/ml). Cultures were maintained at 37° C. in a humidified 95% air/5% $CO_2$ atmosphere. Ganglion non-neuronal cells were eliminated by treatment with araC (10 μM) on days 1 and 3 of culture. Cultures were fed 3 times/week and were routinely used for binding assays within 2 weeks.

MG87/CNTFR is a fibroblast cell line transfected with the human CNTFα receptor gene (Squinto, et al., 1990, Neuron 5:757–766; Davis et al., 1991, Science 253:59–63).

Binding Assays

Binding was performed directly on cell monolayers. Cells in culture wells were washed once with assay buffer consisting of phosphate buffered saline (PBS; pH 7.4), 0.1 mM bacitracin, 1 mM PMSF, 1 μg/ml leupeptin, and 1 mg/ml BSA. After incubation with $^{125}$I-CNTF for 2 hours at room temperature, cells were quickly washed twice with assay buffer, lysed with PBS containing 1% SDS and counted in a Packard Gamma Counter. Non-specific binding was determined in the presence of 1,000-fold excess of unlabelled CNTF. Specific binding towards MG87/CNTFR was 80–90%. Data were analyzed using the GRAPHPAD program (ISI, Philadelphia, Pa.).

Results

Figure 4A:
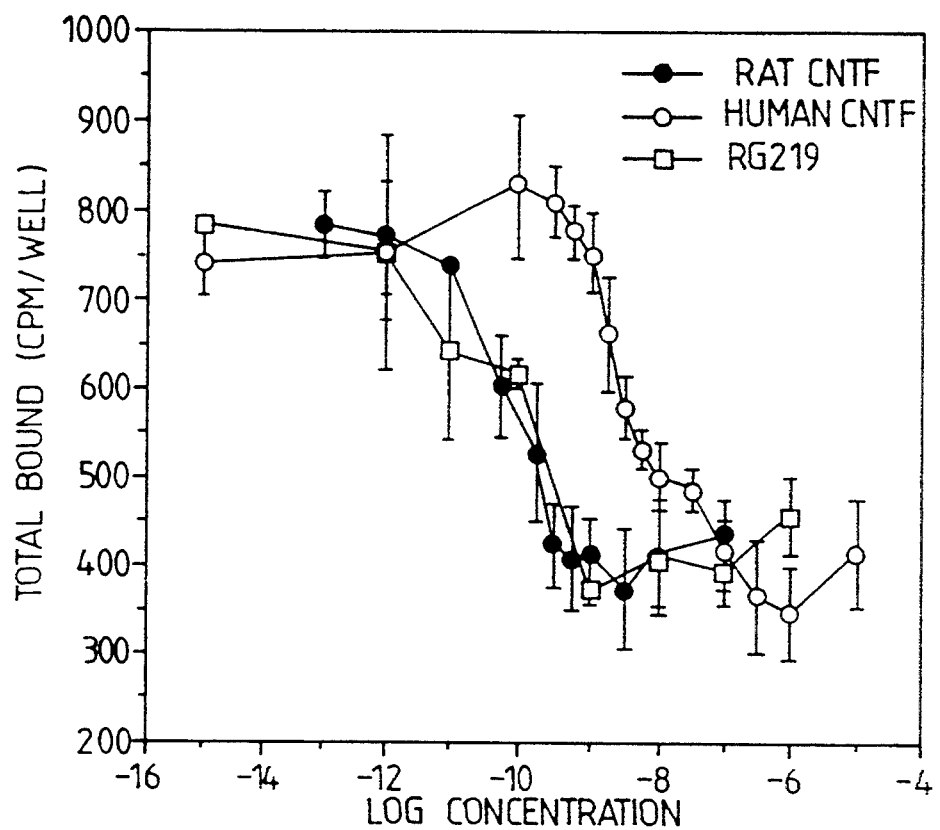
FIG. 4A and 4B. Competitive ligand binding towards A.) SCG neurons and B.) MG87/huCNTFR fibroblasts. Standard deviation from the mean of three determinations is shown by vertical bars.

Competition curves of purified recombinant human, rat and CNTF RPN219 towards $^{125}$I-rat CNTF for binding on rat SCG neurons are shown in FIG. 4a. Both rat and human CNTF complete with $^{125}$I-rat CNTF for binding to SCG neurons, but human CNTF (IC50=25 nM) is 90 times less potent in displacing $^{125}$I-rat CNTF binding than unlabelled rat CNTF (IC50=0.28 nM). In contrast, RPN219 is almost as potent as rat CNTF and clearly more potent than human CNTF (IC50=0.3 nM).

Figure 4B:
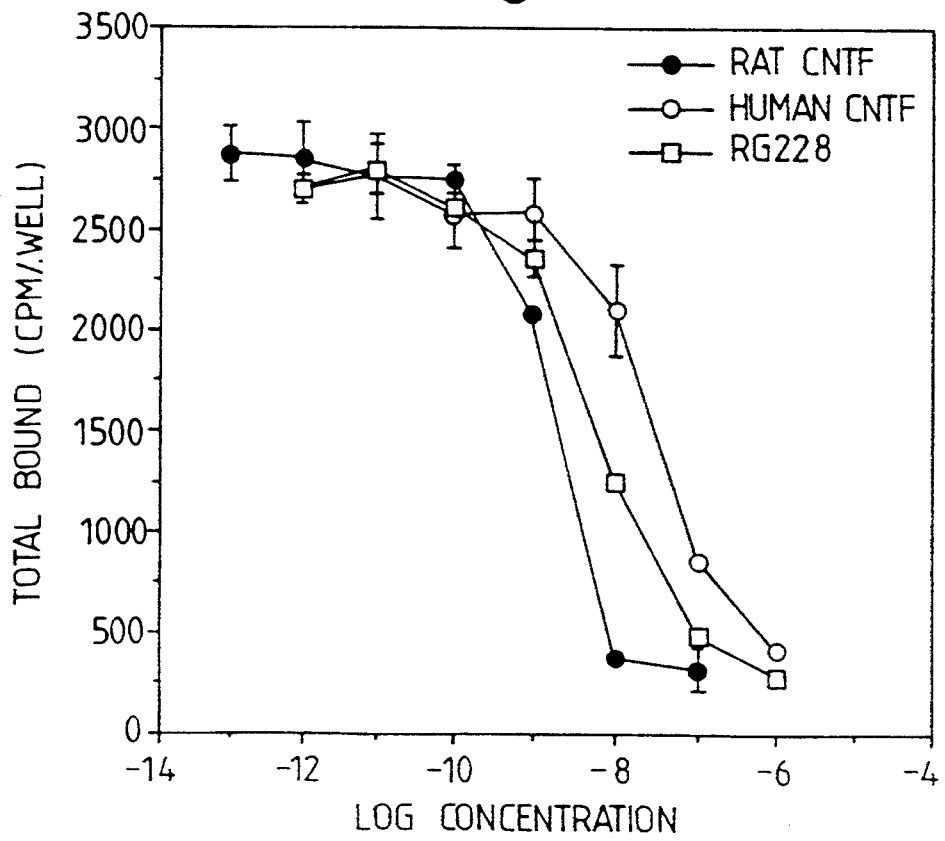

Similar results were obtained from competition experiments with mouse fibroblasts transfected with a plasmid directing the expression of the human CNTF receptor (FIG. 4b). Both rat, human and RPN228 complete with $^{125}$I-rat CNTF for binding to MG87/CNTF cells. Human CNTF (IC50=30 nM) is 12 times less potent than rat CNTF (IC50=2.8 nM), whereas RPN228 is clearly more potent than the human protein (IC50=5.6 nM).

Competition binding experiments with the other modified CNTF proteins shown in FIG. 1 also demonstrated that proteins having R63 displayed the biological activity of rat CNTF, whereas proteins having Q63 displayed the binding properties of human CNTF (data not shown). These results indicate that the single amino acid substitution (Q63→R) is sufficient to confer to human CNTF the receptor binding properties characteristic of rat CNTF.

EXAMPLE 3

Measurement of Biological activity of Modified CNTF Molecules

Materials and Methods

Recombinant CNTF was assayed on dissociated cultures of chick ciliary ganglion (CG) neurons as described (Masiakowski et al. 1991, id.), except that surviving cells were stained with MTT (Mosmann, T. 1983; J. Immunol. Methods 65:55–63).

Results

Figure 3B:
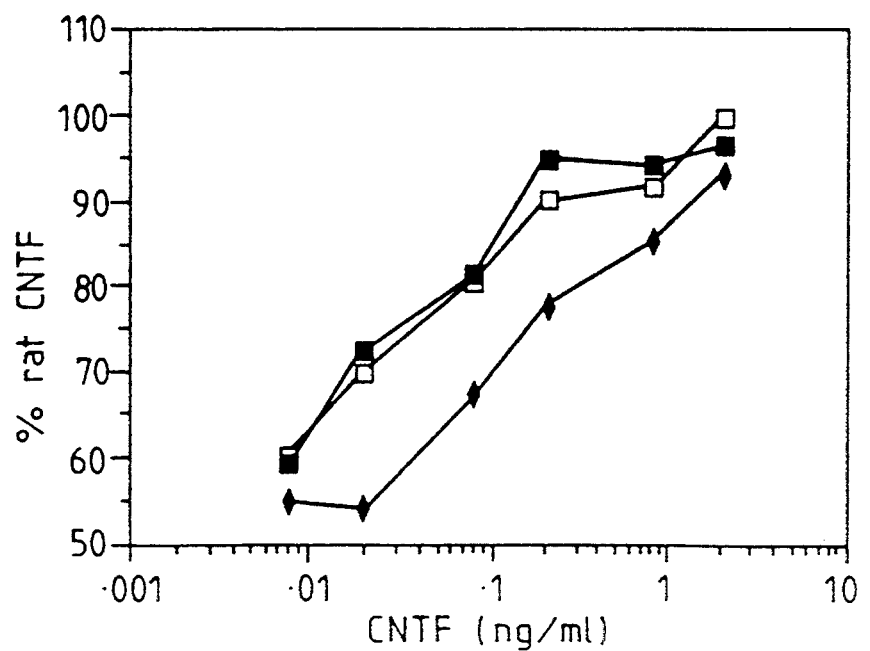

FIG. 3 shows dose-response curves of dissociated, neuronenriched cultures of E8 chick embryo ciliary ganglia for purified recombinant human, rat and the modified CNTF proteins RPN219 and RPN228. By this assay, the biological activity of the chimeric proteins is indistinguishable from that of purified recombinant rat CNTF and clearly higher than that of recombinant human CNTF. Comparison of the dose-response curves in FIG. 3 also shows that the maximal levels of surviving neurons obtained with RPN219, RPN228 or rat CNTF are higher than those obtained with human CNTF. These results suggest that RPN219 and RPN228, like rat CNTF, are active towards a larger population of neurons than human CNTF. In parallel experiments, the biological activity of the other modified CNTF proteins shown in FIG. 1 was examined. In every case, modified CNTF proteins carrying the (Q63→R) substitution displayed the biological activity of rat CNTF whereas proteins having Q63 displayed the activity of human CNTF (data not shown).

Overall, these results indicate that the single amino acid substitution (Q63→R) is sufficient to confer to human CNTF the biological activity of rat CNTF.

EXAMPLE 4

Use of Modified CNTF To Prevent Light Induced Photoreceptor Injury

Albino rats of either the F344 or Sprague-Dawley strain were used at 2–5 months of age. The rats were maintained in a cyclic light environment (12 hr on: 12 hr off at an in-cage illuminance of less than 25 ft-c) for 9 or more days before being exposed to constant light. The rats were exposed to 1 or 2 weeks of constant light at an illuminance level of 115–200 ft-c (most rats received 125–170 ft-c) provided by two 40 watt General Electric "cool-white" fluorescent bulbs with a white reflector that was suspended 60 cm above the floor of the cage. During light exposure, rats were maintained in transparent polycarbonate cages with stainless steel wire-bar covers.

Two days before constant light exposure, rats anesthetized with a ketamine-xylazine mixture were injected intravitreally with 1 μl of rat CNTF, human CNTF or modified CNTF [hCNTF (Q63→R)] dissolved in phosphate buffered saline (PBS) at a concentration of 0.1 to 500 ng/μl. The injections were made with the insertion of a 32 gauge needle through the sclera, choroid and retina approximately midway between the ora serrata and equator of the eye. In all cases, the injections were made into the superior hemisphere of the eye.

Immediately following constant light exposure, the rats were sacrificed by overdose of carbon dioxide followed immediately by vascular perfusion of mixed aldehydes. The eyes were embedded in epoxy resin for sectioning at 1 μm thickness to provide sections of the entire retina along the vertical meridian of the eye. The degree of light-induced retinal degeneration was quantified by assessing the degree of photoreceptor rescue by a 0–4+ pathologist's scale of rescue, 4+ being maximal rescue and almost normal retinal integrity. The degree of photoreceptor rescue in each section, as based on comparison to the control eye in the same rat, was scored by four individuals. This method has the advantage of considering not only the ONL thickness, but also more subtle degenerative changes to the photoreceptor inner and outer segments, as well as spatial degenerative gradients within the eye. Three eyes were examined for each time point to generate a dose response curve.

Results

The degree of rescue was measured for human, rat and hCNTF (Q63→R). The data indicated that both rat and hCNTF (Q63→R) had tenfold greater ability to rescue photoreceptors in the light damage model than did recombinant human CNTF.

It is to be understood that while the invention has been described above in conjunction with preferred specific embodiments, the description and examples are intended to illustrate and not limit the scope of the invention, which is defined by the scope of the appended claims.

---

I claim:

1. Modified human ciliary neurotrophic factor comprising human ciliary neurotrophic factor having the modification Gln63→Arg.

2. Modified ciliary neurotrophic factor according to claim 1 selected from the group consisting of SEQ ID NO:6, SEQ ID NO:9 SEQ ID NO:11, SEQ ID NO:12, and SEQ ID NO:15.

3. A composition comprising a substantially pure modified ciliary neurotrophic factor according to claim 1 or 2 and a carrier.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
      ( A ) LENGTH: 200 amino acids
      ( B ) TYPE: amino acid
      ( C ) STRANDEDNESS: single
      ( D ) TOPOLOGY: unknown ( i i ) MOLECULE TYPE: protein ( x i ) SEQUENCE DESCRIPTION: SEQ ID NO:1:

```
Met Ala Phe Thr Glu His Ser Pro Leu Thr Pro His Arg Arg Asp Leu
  1               5                  10                  15
Cys Ser Arg Ser Ile Trp Leu Ala Arg Lys Ile Arg Ser Asp Leu Thr
             20                  25                  30
Ala Leu Thr Glu Ser Tyr Val Lys His Gln Gly Leu Asn Lys Asn Ile
             35                  40                  45
Asn Leu Asp Ser Ala Asp Gly Met Pro Val Ala Ser Thr Asp Gln Trp
     50                  55                  60
Ser Glu Leu Thr Glu Ala Glu Arg Leu Gln Glu Asn Leu Gln Ala Tyr
 65                  70                  75                  80
Arg Thr Phe His Val Leu Leu Ala Arg Leu Leu Glu Asp Gln Gln Val
                 85                  90                  95
His Phe Thr Pro Thr Glu Gly Asp Phe His Gln Ala Ile His Thr Leu
                100                 105                 110
```

```
        Leu  Leu  Gln  Val  Ala  Ala  Phe  Ala  Tyr  Gln  Ile  Glu  Glu  Leu  Met  Ile
                  115                      120                 125

Leu  Leu  Glu  Tyr  Lys  Ile  Pro  Arg  Asn  Glu  Ala  Asp  Gly  Met  Pro  Ile
                  130                      135                 140

Asn  Val  Gly  Asp  Gly  Gly  Leu  Phe  Glu  Lys  Lys  Leu  Trp  Gly  Leu  Lys
        145                      150                      155                      160

Val  Leu  Gln  Glu  Leu  Ser  Gln  Trp  Thr  Val  Arg  Ser  Ile  His  Asp  Leu
                            165                      170                      175

Arg  Phe  Ile  Ser  Ser  His  Gln  Thr  Gly  Ile  Pro  Ala  Arg  Gly  Ser  His
                       180                      185                      190

Tyr  Ile  Ala  Asn  Asn  Lys  Lys  Met
                       195                      200
```

( 2 ) INFORMATION FOR SEQ ID NO:2:

( i ) SEQUENCE CHARACTERISTICS:
        ( A ) LENGTH: 200 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:2:

```
        Met  Ala  Phe  Ala  Glu  Gln  Thr  Pro  Leu  Thr  Leu  His  Arg  Arg  Asp  Leu
        1                   5                        10                      15

Cys  Ser  Arg  Ser  Ile  Trp  Leu  Ala  Arg  Lys  Ile  Arg  Ser  Asp  Leu  Thr
                       20                      25                      30

Ala  Leu  Met  Glu  Ser  Tyr  Val  Lys  His  Gln  Gly  Leu  Asn  Lys  Asn  Ile
                  35                      40                      45

Asn  Leu  Asp  Ser  Val  Asp  Gly  Val  Pro  Val  Ala  Ser  Thr  Asp  Arg  Trp
             50                      55                      60

Ser  Glu  Met  Thr  Glu  Ala  Glu  Arg  Leu  Gln  Glu  Asn  Leu  Gln  Ala  Tyr
        65                       70                      75                      80

Arg  Thr  Phe  Gln  Gly  Met  Leu  Thr  Lys  Leu  Leu  Glu  Asp  Gln  Arg  Val
                            85                      90                      95

His  Phe  Thr  Pro  Thr  Glu  Gly  Asp  Phe  His  Gln  Ala  Ile  His  Thr  Leu
                       100                     105                     110

Met  Leu  Gln  Val  Asp  Ala  Phe  Ala  Tyr  Gln  Leu  Glu  Glu  Leu  Met  Val
                  115                     120                     125

Leu  Leu  Glu  Gln  Lys  Ile  Pro  Glu  Asn  Glu  Ala  Asp  Gly  Met  Pro  Ala
                  130                     135                     140

Thr  Val  Gly  Asp  Gly  Gly  Leu  Phe  Glu  Lys  Lys  Leu  Trp  Gly  Leu  Lys
        145                      150                     155                      160

Val  Leu  Gln  Glu  Leu  Ser  Gln  Trp  Thr  Val  Arg  Ser  Ile  His  Asp  Leu
                            165                     170                      175

Arg  Val  Ile  Ser  Ser  His  Gln  Met  Gly  Ile  Ser  Ala  Leu  Glu  Ser  His
                       180                     185                      190

Tyr  Gly  Ala  Lys  Asp  Lys  Gln  Met
                       195                     200
```

( 2 ) INFORMATION FOR SEQ ID NO:3:

( i ) SEQUENCE CHARACTERISTICS:
        ( A ) LENGTH: 199 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:3:

```
Met  Ala  Phe  Met  Glu  His  Ser  Ala  Leu  Thr  Pro  His  Arg  Arg  Glu  Leu
 1              5                        10                       15

Cys  Ser  Arg  Thr  Ile  Trp  Leu  Ala  Arg  Lys  Ile  Arg  Ser  Asp  Leu  Thr
               20                  25                       30

Ala  Leu  Thr  Glu  Ser  Tyr  Val  Lys  His  Gln  Gly  Leu  Asn  Lys  Asn  Ile
          35                       40                       45

Asn  Leu  Asp  Ser  Val  Asp  Gly  Val  Pro  Met  Ala  Ser  Thr  Asp  Gln  Trp
     50                       55                       60

Ser  Glu  Leu  Thr  Glu  Ala  Glu  Arg  Leu  Gln  Glu  Asn  Leu  Gln  Ala  Tyr
 65                      70                       75                        80

Arg  Thr  Phe  His  Ile  Met  Leu  Ala  Arg  Leu  Leu  Glu  Asp  Gln  Gln  Val
               85                       90                       95

His  Phe  Thr  Pro  Ala  Glu  Gly  Asp  His  Phe  Gln  Ala  Ile  His  Thr  Leu
              100                      105                      110

Leu  Leu  Gln  Val  Ala  Ala  Phe  Ala  Tyr  Gln  Ile  Glu  Glu  Leu  Met  Val
              115                      120                      125

Leu  Leu  Glu  Cys  Asn  Ile  Pro  Pro  Lys  Asp  Ala  Asp  Gly  Thr  Pro  Val
              130                      135                      140

Ile  Gly  Gly  Asp  Gly  Leu  Phe  Glu  Lys  Lys  Leu  Trp  Gly  Leu  Lys  Val
145                            150                      155                      160

Leu  Gln  Glu  Leu  Ser  His  Trp  Thr  Val  Arg  Ser  Ile  His  Asp  Leu  Arg
               165                      170                      175

Val  Ile  Ser  Cys  His  Gln  Thr  Gly  Ile  Pro  Ala  His  Gly  Ser  His  Tyr
               180                      185                      190

Ile  Ala  Asn  Asp  Lys  Glu  Met
               195
```

( 2 ) INFORMATION FOR SEQ ID NO:4:

( i ) SEQUENCE CHARACTERISTICS:
        ( A ) LENGTH: 186 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:4:

```
Met  Ala  Phe  Ala  Glu  Gln  Ser  Pro  Leu  Thr  Leu  His  Arg  Arg  Asp  Leu
 1              5                        10                       15

Cys  Ser  Arg  Ser  Ile  Trp  Leu  Ala  Arg  Lys  Ile  Arg  Ser  Asp  Leu  Thr
               20                  25                       30

Ala  Leu  Met  Glu  Ser  Tyr  Val  Lys  His  Gln  Gly  Leu  Asn  Lys  Asn  Ile
          35                       40                       45

Ser  Leu  Asp  Ser  Val  Asp  Pro  Val  Ala  Ser  Thr  Asp  Arg  Trp  Ser  Glu
     50                       55                       60

Met  Thr  Glu  Ala  Glu  Arg  Leu  Gln  Glu  Asn  Leu  Gln  Ala  Tyr  Arg  Gln
 65                      70                       75                        80

Gly  Met  Leu  Thr  Arg  Leu  Leu  Glu  Asp  Gln  Arg  Val  His  Phe  Thr  Pro
               85                       90                       95

Thr  Glu  Gly  Asp  Phe  His  Gln  Ala  His  Thr  Leu  Thr  Gln  Val  Ser  Ala
              100                      105                      110

Phe  Ala  Tyr  Gln  Leu  Glu  Glu  Leu  Met  Ala  Leu  Leu  Glu  Gln  Lys  Val
              115                      120                      125

Asn  Glu  Ala  Asp  Gly  Met  Pro  Val  Thr  Ile  Gly  Asp  Gly  Gly  Leu  Phe
              130                      135                      140

Glu  Lys  Leu  Trp  Gly  Leu  Lys  Val  Leu  Leu  Ser  Gln  Trp  Thr  Val  Arg
```

|  145 |  | | | 150 | | | | 155 | | | | 160 |

Ser Ile His Asp Leu Arg Val Ile Ser Ser His His Met Gly Ile Ser
              165                     170                 175

Ala His Ser His Tyr Gly Ala Lys Gln Met
              180                 185

( 2 ) INFORMATION FOR SEQ ID NO:5:

( i ) SEQUENCE CHARACTERISTICS:
        ( A ) LENGTH: 195 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:5:

Met Ala Ala Ala Asp Thr Pro Ser Ala Thr Leu Arg His His Asp Leu
1               5                   10                  15

Cys Ser Arg Gly Ile Arg Leu Ala Arg Lys Met Arg Ser Asp Val Thr
              20                  25                  30

Asp Leu Leu Asp Ile Tyr Val Glu Arg Gln Gly Leu Asp Ala Ser Ile
              35                  40                  45

Ser Val Ala Ala Val Asp Gly Val Pro Thr Ala Ala Val Glu Arg Trp
    50                  55                  60

Ala Glu Gln Thr Gly Thr Gln Arg Leu Leu Asp Asn Leu Ala Ala Tyr
65                  70                  75                  80

Arg Ala Phe Arg Thr Leu Leu Ala Gln Met Leu Glu Glu Gln Arg Glu
              85                  90                  95

Leu Leu Gly Asp Thr Asp Ala Glu Leu Gly Pro Ala Leu Ala Ala Met
              100                 105                 110

Leu Leu Gln Val Ser Ala Phe Val Tyr His Leu Glu Glu Leu Leu Glu
              115                 120                 125

Leu Glu Ser Arg Gly Ala Pro Ala Glu Glu Gly Ser Glu Pro Pro Ala
              130                 135                 140

Pro Pro Arg Leu Ser Leu Phe Glu Gln Lys Leu Arg Gly Leu Arg Val
145                 150                 155                 160

Leu Arg Glu Leu Ala Gln Trp Ala Val Arg Ser Val Arg Asp Leu Arg
              165                 170                 175

Gln Leu Ser Lys His Gly Pro Gly Ser Gly Ala Ala Leu Gly Leu Pro
              180                 185                 190

Glu Ser Gln
    195

( 2 ) INFORMATION FOR SEQ ID NO:6:

( i ) SEQUENCE CHARACTERISTICS:
        ( A ) LENGTH: 200 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:6:

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
              20                  25                  30

Ala Leu Thr Glu Ser Tyr Val Lys His Gln Gly Leu Asn Lys Asn Ile
              35                  40                  45

```
Asn  Leu  Asp  Ser  Val  Asp  Gly  Val  Pro  Val  Ala  Ser  Thr  Asp  Arg  Trp
     50                  55                       60

Ser  Glu  Met  Thr  Glu  Ala  Glu  Arg  Leu  Gln  Glu  Asn  Leu  Gln  Ala  Tyr
65                       70                  75                            80

Arg  Thr  Phe  Gln  Gly  Met  Leu  Thr  Lys  Leu  Leu  Glu  Asp  Gln  Arg  Val
               85                       90                            95

His  Phe  Thr  Pro  Thr  Glu  Gly  Asp  Phe  His  Gln  Ala  Ile  His  Thr  Leu
              100                      105                          110

Met  Leu  Gln  Val  Ser  Ala  Phe  Ala  Tyr  Gln  Leu  Glu  Glu  Leu  Met  Val
         115                      120                       125

Leu  Leu  Glu  Gln  Lys  Ile  Pro  Glu  Asn  Glu  Ala  Asp  Gly  Met  Pro  Ala
         130                 135                      140

Thr  Val  Gly  Asp  Gly  Gly  Leu  Phe  Glu  Lys  Lys  Leu  Trp  Gly  Leu  Lys
145                      150                  155                            160

Val  Leu  Gln  Glu  Leu  Ser  Gln  Trp  Thr  Val  Arg  Ser  Ile  His  Asp  Leu
                165                      170                           175

Arg  Val  Ile  Ser  Ser  His  Gln  Met  Gly  Ile  Ser  Ala  Leu  Glu  Ser  His
              180                      185                          190

Tyr  Gly  Ala  Lys  Asp  Lys  Gln  Met
         195                      200
```

( 2 ) INFORMATION FOR SEQ ID NO:7:

( i ) SEQUENCE CHARACTERISTICS:
        ( A ) LENGTH: 200 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:7:

```
Met  Ala  Phe  Ala  Glu  Gln  Thr  Pro  Leu  Thr  Leu  His  Arg  Arg  Asp  Leu
1                   5                        10                            15

Cys  Ser  Arg  Ser  Ile  Trp  Leu  Ala  Arg  Lys  Ile  Arg  Ser  Asp  Leu  Thr
              20                       25                       30

Ala  Leu  Met  Glu  Ser  Tyr  Val  Lys  His  Gln  Gly  Leu  Asn  Lys  Asn  Ile
         35                       40                           45

Asn  Leu  Asp  Ser  Ala  Asp  Gly  Met  Pro  Val  Ala  Ser  Thr  Asp  Gln  Trp
     50                  55                       60

Ser  Glu  Leu  Thr  Glu  Ala  Glu  Arg  Leu  Gln  Glu  Asn  Leu  Gln  Ala  Tyr
65                       70                  75                            80

Arg  Thr  Phe  His  Val  Leu  Leu  Ala  Arg  Leu  Leu  Glu  Asp  Gln  Gln  Val
               85                       90                            95

His  Phe  Thr  Pro  Thr  Glu  Gly  Asp  Phe  His  Gln  Ala  Ile  His  Thr  Leu
              100                      105                          110

Leu  Leu  Gln  Val  Ala  Ala  Phe  Ala  Tyr  Gln  Ile  Glu  Glu  Leu  Met  Ile
         115                      120                       125

Leu  Leu  Glu  Tyr  Lys  Ile  Pro  Arg  Asn  Glu  Ala  Asp  Gly  Met  Pro  Ile
         130                 135                      140

Asn  Val  Gly  Asp  Gly  Gly  Leu  Phe  Glu  Lys  Lys  Leu  Trp  Gly  Leu  Lys
145                      150                  155                            160

Val  Leu  Gln  Glu  Leu  Ser  Gln  Trp  Thr  Val  Arg  Ser  Ile  His  Asp  Leu
                165                      170                           175

Arg  Phe  Ile  Ser  Ser  His  Gln  Thr  Gly  Ile  Pro  Ala  Arg  Gly  Ser  His
              180                      185                          190

Tyr  Ile  Ala  Asn  Asn  Lys  Lys  Met
         195                      200
```

(2) INFORMATION FOR SEQ ID NO:8:

(i) SEQUENCE CHARACTERISTICS:
        (A) LENGTH: 200 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:8:

```
Met Ala Phe Thr Glu His Ser Pro Leu Thr Pro His Arg Arg Asp Leu
 1               5                  10                  15

Cys Ser Arg Ser Ile Trp Leu Ala Arg Lys Ile Arg Ser Asp Leu Thr
                20                  25                  30

Ala Leu Thr Glu Ser Tyr Val Lys His Gln Gly Leu Asn Lys Asn Ile
            35                  40                  45

Asn Leu Asp Ser Ala Asp Gly Met Pro Val Ala Ser Thr Asp Gln Trp
        50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
                100                 105                 110

Leu Leu Gln Val Ala Ala Phe Ala Tyr Gln Ile Glu Glu Leu Met Ile
            115                 120                 125

Leu Leu Glu Tyr Lys Ile Pro Arg Asn Glu Ala Asp Gly Met Pro Ile
        130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Val Ile Ser Ser His Gln Met Gly Ile Ser Ala Leu Glu Ser His
                180                 185                 190

Tyr Gly Ala Lys Asp Lys Gln Met
            195                 200
```

(2) INFORMATION FOR SEQ ID NO:9:

(i) SEQUENCE CHARACTERISTICS:
        (A) LENGTH: 200 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:9:

```
Met Ala Phe Ala Glu Gln Thr Pro Leu Thr Leu His Arg Arg Asp Leu
 1               5                  10                  15

Cys Ser Arg Ser Ile Trp Leu Ala Arg Lys Ile Arg Ser Asp Leu Thr
                20                  25                  30

Ala Leu Met Glu Ser Tyr Val Lys His Gln Gly Leu Asn Lys Asn Ile
            35                  40                  45

Asn Leu Asp Ser Val Asp Gly Val Pro Val Ala Ser Thr Asp Arg Trp
        50                  55                  60

Ser Glu Met Thr Glu Ala Glu Arg Leu Gln Glu Asn Leu Gln Ala Tyr
65                  70                  75                  80

Arg Thr Phe Gln Gly Met Leu Thr Lys Leu Leu Glu Asp Gln Arg Val
                85                  90                  95
```

```
His  Phe  Thr  Pro  Thr  Glu  Gly  Asp  Phe  His  Gln  Ala  Ile  His  Thr  Leu
               100                      105                      110

Met  Leu  Gln  Val  Ser  Ala  Phe  Ala  Tyr  Gln  Leu  Glu  Glu  Leu  Met  Val
               115                      120                      125

Leu  Leu  Glu  Gln  Lys  Ile  Pro  Glu  Asn  Glu  Ala  Asp  Gly  Met  Pro  Ala
          130                      135                      140

Thr  Val  Gly  Asp  Gly  Gly  Leu  Phe  Glu  Lys  Lys  Leu  Trp  Gly  Leu  Lys
145                           150                 155                      160

Val  Leu  Gln  Glu  Leu  Ser  Gln  Trp  Thr  Val  Arg  Ser  Ile  His  Asp  Leu
                    165                      170                      175

Arg  Phe  Ile  Ser  Ser  His  Gln  Thr  Gly  Ile  Pro  Ala  Arg  Gly  Ser  His
               180                      185                      190

Tyr  Ile  Ala  Asn  Asn  Lys  Lys  Met
          195                 200
```

( 2 ) INFORMATION FOR SEQ ID NO:10:

( i ) SEQUENCE CHARACTERISTICS:
        ( A ) LENGTH: 200 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:10:

```
Met  Ala  Phe  Thr  Glu  His  Ser  Pro  Leu  Thr  Pro  His  Arg  Arg  Asp  Leu
1                   5                   10                       15

Cys  Ser  Arg  Ser  Ile  Trp  Leu  Ala  Arg  Lys  Ile  Arg  Ser  Asp  Leu  Thr
               20                      25                       30

Ala  Leu  Thr  Glu  Ser  Tyr  Val  Lys  His  Gln  Gly  Leu  Asn  Lys  Asn  Ile
               35                      40                       45

Asn  Leu  Asp  Ser  Ala  Asp  Gly  Met  Pro  Val  Ala  Ser  Thr  Asp  Gln  Trp
     50                      55                       60

Ser  Glu  Leu  Thr  Glu  Ala  Glu  Arg  Leu  Gln  Glu  Asn  Leu  Gln  Ala  Tyr
65                       70                       75                       80

Arg  Thr  Phe  Gln  Gly  Met  Leu  Thr  Lys  Leu  Leu  Glu  Asp  Gln  Arg  Val
               85                      90                       95

His  Phe  Thr  Pro  Thr  Glu  Gly  Asp  Phe  His  Gln  Ala  Ile  His  Thr  Leu
               100                     105                      110

Met  Leu  Gln  Val  Ser  Ala  Phe  Ala  Tyr  Gln  Leu  Glu  Glu  Leu  Met  Val
               115                     120                      125

Leu  Leu  Glu  Gln  Lys  Ile  Pro  Glu  Asn  Glu  Ala  Asp  Gly  Met  Pro  Ala
          130                     135                      140

Thr  Val  Gly  Asp  Gly  Gly  Leu  Phe  Glu  Lys  Lys  Leu  Trp  Gly  Leu  Lys
145                           150                 155                      160

Val  Leu  Gln  Glu  Leu  Ser  Gln  Trp  Thr  Val  Arg  Ser  Ile  His  Asp  Leu
                    165                      170                      175

Arg  Phe  Ile  Ser  Ser  His  Gln  Thr  Gly  Ile  Pro  Ala  Arg  Gly  Ser  His
               180                      185                      190

Tyr  Ile  Ala  Asn  Asn  Lys  Lys  Met
          195                 200
```

( 2 ) INFORMATION FOR SEQ ID NO:11:

( i ) SEQUENCE CHARACTERISTICS:
        ( A ) LENGTH: 200 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:11:

```
Met Ala Phe Thr Glu His Ser Pro Leu Thr Pro His Arg Arg Asp Leu
 1               5                  10                  15

Cys Ser Arg Ser Ile Trp Leu Ala Arg Lys Ile Arg Ser Asp Leu Thr
             20                  25                  30

Ala Leu Met Glu Ser Tyr Val Lys His Gln Gly Leu Asn Lys Asn Ile
         35                  40                  45

Asn Leu Asp Ser Val Asp Gly Val Pro Val Ala Ser Thr Asp Arg Trp
     50                  55                  60

Ser Glu Met Thr Glu Ala Glu Arg Leu Gln Glu Asn Leu Gln Ala Tyr
 65                  70                  75                  80

Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
             100                 105                 110

Leu Leu Gln Val Ala Ala Phe Ala Tyr Gln Ile Glu Glu Leu Met Ile
         115                 120                 125

Leu Leu Glu Tyr Lys Ile Pro Arg Asn Glu Ala Asp Gly Met Pro Ile
     130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                 165                 170                 175

Arg Phe Ile Ser Ser His Gln Thr Gly Ile Pro Ala Arg Gly Ser His
             180                 185                 190

Tyr Ile Ala Asn Asn Lys Lys Met
         195                 200
```

( 2 ) INFORMATION FOR SEQ ID NO:12:

( i ) SEQUENCE CHARACTERISTICS:
( A ) LENGTH: 200 amino acids
( B ) TYPE: amino acid
( C ) STRANDEDNESS: single
( D ) TOPOLOGY: unknown ( i i ) MOLECULE TYPE: protein ( x i ) SEQUENCE DESCRIPTION: SEQ ID NO:12:

```
Met Ala Phe Thr Glu His Ser Pro Leu Thr Pro His Arg Arg Asp Leu
 1               5                  10                  15

Cys Ser Arg Ser Ile Trp Leu Ala Arg Lys Ile Arg Ser Asp Leu Thr
             20                  25                  30

Ala Leu Thr Glu Ser Tyr Val Lys His Gln Gly Leu Asn Lys Asn Ile
         35                  40                  45

Asn Leu Asp Ser Val Asp Gly Val Pro Val Ala Ser Thr Asp Arg Trp
     50                  55                  60

Ser Glu Met Thr Glu Ala Glu Arg Leu Gln Glu Asn Leu Gln Ala Tyr
 65                  70                  75                  80

Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
             100                 105                 110

Leu Leu Gln Val Ala Ala Phe Ala Tyr Gln Ile Glu Glu Leu Met Ile
         115                 120                 125

Leu Leu Glu Tyr Lys Ile Pro Arg Asn Glu Ala Asp Gly Met Pro Ile
```

|   |   |   |   | 130 |   |   |   |   | 135 |   |   |   |   | 140 |   |
|---|---|---|---|---|---|---|---|---|---|---|---|---|---|---|---|

Asn Val Gly Asp Gly Gly Leu Phe Glu Lys Lys Leu Trp Gly Leu Lys
145                     150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
            195             200

( 2 ) INFORMATION FOR SEQ ID NO:13:

( i ) SEQUENCE CHARACTERISTICS:
        ( A ) LENGTH: 200 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:13:

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
                20                  25                  30

Ala Leu Thr Glu Ser Tyr Val Lys His Gln Gly Leu Asn Lys Asn Ile
            35                  40                  45

Asn Leu Asp Ser Val Asp Gly Met Pro Val Ala Ser Thr Asp Gln Trp
        50              55                  60

Ser Glu Met Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
            85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
            115                 120                 125

Leu Leu Glu Tyr Lys Ile Pro Arg Asn Glu Ala Asp Gly Met Pro Ile
            130                 135                 140

Asn Val Gly Asp Gly Gly Leu Phe Glu Lys Lys Leu Trp Gly Leu Lys
145                     150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
            195             200

( 2 ) INFORMATION FOR SEQ ID NO:14:

( i ) SEQUENCE CHARACTERISTICS:
        ( A ) LENGTH: 200 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:14:

Met Ala Phe Thr Glu His Ser Pro Leu Thr Pro His Arg Arg Asp Leu
1               5                   10                  15

```
        Cys   Ser   Arg   Ser   Ile   Trp   Leu   Ala   Arg   Lys   Ile   Arg   Ser   Asp   Leu   Thr
                          20                            25                            30

Ala   Leu   Thr   Glu   Ser   Tyr   Val   Lys   His   Gln   Gly   Leu   Asn   Lys   Asn   Ile
                    35                            40                            45

Asn   Leu   Asp   Ser   Val   Asp   Gly   Val   Pro   Val   Ala   Ser   Thr   Asp   Gln   Trp
              50                            55                            60

Ser   Glu   Leu   Thr   Glu   Ala   Glu   Arg   Leu   Gln   Glu   Asn   Leu   Gln   Ala   Tyr
        65                            70                            75                            80

Arg   Thr   Phe   His   Val   Leu   Leu   Ala   Arg   Leu   Leu   Glu   Asp   Gln   Gln   Val
                                85                            90                            95

His   Phe   Thr   Pro   Thr   Glu   Gly   Asp   Phe   His   Gln   Ala   Ile   His   Thr   Leu
                          100                           105                           110

Leu   Leu   Gln   Val   Ala   Ala   Phe   Ala   Tyr   Gln   Ile   Glu   Glu   Leu   Met   Ile
                    115                           120                           125

Leu   Leu   Glu   Tyr   Lys   Ile   Pro   Arg   Asn   Glu   Ala   Asp   Gly   Met   Pro   Ile
              130                           135                           140

Asn   Val   Gly   Asp   Gly   Gly   Leu   Phe   Glu   Lys   Lys   Leu   Trp   Gly   Leu   Lys
        145                           150                           155                           160

Val   Leu   Gln   Glu   Leu   Ser   Gln   Trp   Thr   Val   Arg   Ser   Ile   His   Asp   Leu
                          165                           170                           175

Arg   Phe   Ile   Ser   Ser   His   Gln   Thr   Gly   Ile   Pro   Ala   Arg   Gly   Ser   His
                          180                           185                           190

Tyr   Ile   Ala   Asn   Asn   Lys   Lys   Met
                    195                           200
```

( 2 ) INFORMATION FOR SEQ ID NO:15:

( i ) SEQUENCE CHARACTERISTICS:
       ( A ) LENGTH: 200 amino acids
       ( B ) TYPE: amino acid
       ( C ) STRANDEDNESS: single
       ( D ) TOPOLOGY: unknown ( i i ) MOLECULE TYPE: protein ( x i ) SEQUENCE DESCRIPTION: SEQ ID NO:15:

```
        Met   Ala   Phe   Thr   Glu   His   Ser   Pro   Leu   Thr   Pro   His   Arg   Arg   Asp   Leu
        1                 5                             10                            15

Cys   Ser   Arg   Ser   Ile   Trp   Leu   Ala   Arg   Lys   Ile   Arg   Ser   Asp   Leu   Thr
                          20                            25                            30

Ala   Leu   Thr   Glu   Ser   Tyr   Val   Lys   His   Gln   Gly   Leu   Asn   Lys   Asn   Ile
                    35                            40                            45

Asn   Leu   Asp   Ser   Ala   Asp   Gly   Met   Pro   Val   Ala   Ser   Thr   Asp   Arg   Trp
              50                            55                            60

Ser   Glu   Leu   Thr   Glu   Ala   Glu   Arg   Leu   Gln   Glu   Asn   Leu   Gln   Ala   Tyr
        65                            70                            75                            80

Arg   Thr   Phe   His   Val   Leu   Leu   Ala   Arg   Leu   Leu   Glu   Asp   Gln   Gln   Val
                                85                            90                            95

His   Phe   Thr   Pro   Thr   Glu   Gly   Asp   Phe   His   Gln   Ala   Ile   His   Thr   Leu
                          100                           105                           110

Leu   Leu   Gln   Val   Ala   Ala   Phe   Ala   Tyr   Gln   Ile   Glu   Glu   Leu   Met   Ile
                    115                           120                           125

Leu   Leu   Glu   Tyr   Lys   Ile   Pro   Arg   Asn   Glu   Ala   Asp   Gly   Met   Pro   Ile
              130                           135                           140

Asn   Val   Gly   Asp   Gly   Gly   Leu   Phe   Glu   Lys   Lys   Leu   Trp   Gly   Leu   Lys
        145                           150                           155                           160

Val   Leu   Gln   Glu   Leu   Ser   Gln   Trp   Thr   Val   Arg   Ser   Ile   His   Asp   Leu
                          165                           170                           175
```

```
Arg Phe Ile Ser Ser His Gln Thr Gly Ile Pro Ala Arg Gly Ser His
            180                 185                 190

Tyr Ile Ala Asn Asn Lys Lys Met
        195                 200
```

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

```
ACGGTAAGCT TGGAGGTTCT C                                              21
```

( 2 ) INFORMATION FOR SEQ ID NO:17:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

```
TCTATCTGGC TAGCAAGGAA GATTCGTTCA GACCTGACTG CTCTTACG                 48
```

( 2 ) INFORMATION FOR SEQ ID NO:18:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

```
AAGGTACGAT AAGCTTGGAG GTTCTCTTGG AGTCGCTCTG CCTCAGTCAG CTCACTCCAA    60
CGATCAGTG                                                            69
```

( 2 ) INFORMATION FOR SEQ ID NO:19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:19:

```
TCTATCTGGC TAGCAAGGAA G                                              21
```